United States Patent [19]

Savrda et al.

[11] Patent Number: 4,460,503

[45] Date of Patent: Jul. 17, 1984

[54] TUBERCULINE ACTIVE PEPTIDES AND A PROCESS FOR PREPARING SAME BY CHEMICAL SYNTHESIS

[75] Inventors: Jaroslav Savrda, Palaiseau; Hugo David, Sevres, both of France

[73] Assignee: Institut Pasteur, Paris, France

[21] Appl. No.: 475,639

[22] Filed: Mar. 15, 1983

[51] Int. Cl.³ ............................................ C07C 103/52
[52] U.S. Cl. ............................................. 260/112.5 R
[58] Field of Search ................................. 260/112.5 R

[56] References Cited

U.S. PATENT DOCUMENTS

| | | | |
|---|---|---|---|
| 3,812,091 | 5/1974 | Ondetti | 260/112.5 R |
| 3,888,837 | 6/1975 | Tsumita et al. | 260/112.5 R |
| 3,943,119 | 3/1976 | Tsumita et al. | 260/112.5 R |
| 4,290,944 | 9/1981 | Goldberg | 260/112.5 R |
| 4,374,765 | 2/1983 | McGregor | 260/112.5 R |
| 4,376,760 | 3/1983 | Jung et al. | 260/112.5 R |
| 4,390,528 | 6/1983 | Najjar | 260/112.5 R |
| 4,395,404 | 7/1983 | Low et al. | 260/112.5 R |

Primary Examiner—Delbert R. Phillips
Attorney, Agent, or Firm—Oblon, Fisher, Spivak, McClelland & Maier

[57] ABSTRACT

The octapeptide Asp-Gly-Gly-Ser-Glu-Ser-Glu-Gly and the hexadecapeptide Asp-Gly-Gly-Ser-Glu-Ser-Glu-Gly-Lys-Asn-Gly-Ser-Gln-Met-Arg-Leu, part of a tuberculin-active intracellular myobacterial protein, have been synthesized. The synthetic peptides were shown to possess tuberculin activity by their ability to induce a delayed-type allergic reaction in skin tests on *Mycobacterium tuberculosis* sensitized guinea pigs.

4 Claims, No Drawings

TUBERCULINE ACTIVE PEPTIDES AND A PROCESS FOR PREPARING SAME BY CHEMICAL SYNTHESIS

FIELD OF THE INVENTION

The present invention relates to tuberculine active peptides and to a process for preparing same by chemical synthesis.

BACKGROUND OF THE INVENTION

Purified protein derivative (PPD), the partially purified form of tuberculin obtained from the products excreted into the culture medium by Mycobacterium tuberculosis by SEIBERT and GLENN, Am. Rev. Tuberc. 1941, 44, 9–25, is in wide use as a tuberculin-active preparation. It is capable of eliciting a delayed-type allergic reaction when administered intracutaneously to humans or other animals sensitized with tubercle bacilli. This material is, however, a complex mixture of proteins lacking specificity for the diagnosis of tuberculous infection or disease and is improper for the laboratory investigation of cell-mediated immunological phenomena. Thus, subjects infected with unrelated mycobacteria may cross-react with PPD, although these cross-reactions are usually less intense than those obtained in persons infected with tubercle bacilli. The lack of specificity of PPD may be related to the heterogeneous nature of this product and to the presence of antigens shared by the various mycobacterial species. Despite numerous attempts to purify and separate the constituents of PPD, none of the antigens making up PPD has yet been characterized, and the isolation of a monospecific tuberculin has not been achieved. The complexity of PPD, as well as the drastic conditions used for the preparation of this material (120° C./20 lb [ca 9 kg] for 30 min), may account for this lack of success. Moreover, it is possible that single molecules may possess multiple determinants, some of which are shared with a number of molecules found in different species of mycobacteria. Thus, the isolation from human tubercle bacilli and the sequence determination by Kuwabara [cf J. Biol. Chem. 250, p.2556-2562, 1975 "Purification and properties of tuberculine-active protein from Mycobacterium tuberculosis" and same p. 2563-2568"Amino-acid sequence of Tuberculin-active protein from Mycobacterium tuberculosis"] of a tuberculin-active protein, one of intracellular origin, is an important step in the elucidation of the nature of the tuberculin-type mycobacterial antigens. This protein is more potent than PPD and, according to published results, accounts for the total tuberculin activity found in the intracellular proteic content. After enzymatic digestion, a tryptic hexapeptide, Asn-Gly-Ser-Gln-Met-Arg, was found to have residual tuberculin activity in skin tests, more particularly the hexapeptide 70-75 and the nonapeptide 61-69 :

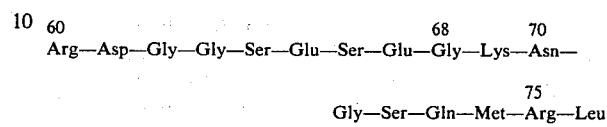

which are part of Kuwabara's protein which is composed of 89 amino-acid residues with the following amino-acid sequence and composition:

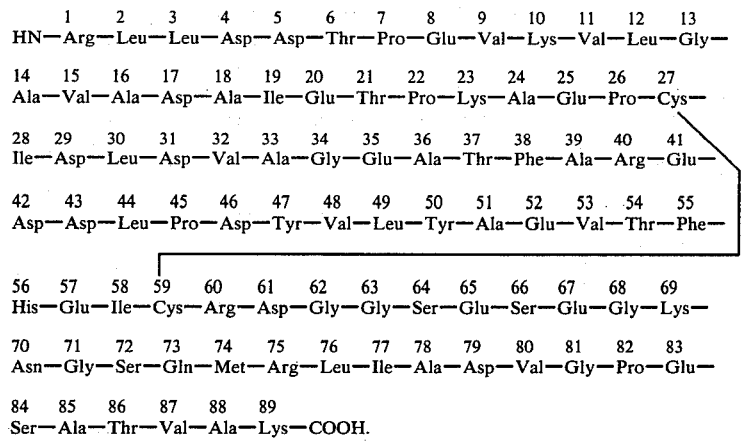

One of the inventors of the present invention [J. SAVRDA, "INFECTION AND IMMUNITY, Dec. 1980, Vol. 30, No. 3, p. 686–693 "Synthesis and biological Assays of a peptide from a Tuberculin-activ protein"] has carried out the chemical synthesis of the heptapeptide Asn-Gly-Ser-Gln-Met-Arg-Leu which is described in said Paper as being performed in 10 steps, starting from $N^\alpha$-BOC-$\omega$-Tos arginine and leucine benzyl ester, in order to ascertain the nature of the determinant responsible for the delayed-type allergic reaction. However, his study has shown that this synthetic heptapeptide is devoid of any tuberculin activity in BCG-infected mice and in skin tests on Mycobacterium tuberculosis-sensitized guinea pigs and has also shown that the purified protein derivative (PPD), that is to say the complex mixture of proteins of unknown composition which is excreted into the culture medium by M. tuberculosis and is in wide use as a tuberculinactive preparation, cross-reacts weakly in radioimmunoassays with the synthetic heptapeptide, when 125 I-labelled heptapeptide and an anti-heptapeptide antiserum are used.

Accordingly, the Inventors have decided to go on with their study in order to synthetise other ones among the peptides included in the protein identified by KUWABARA, with the aim of detecting the one (s) endowed with tuberculin-activity.

SUMMARY OF THE INVENTION

According to the present invention, the octapeptide

Asp-Gly-Gly-Ser-Glu-Ser-Glu-Gly  (I)

the hexadecapeptide

Asp-Gly-Gly-Ser-Glu-Ser-Glu-Gly-Lys-Asn-Gly-Ser-Gln-Met-Arg-Leu  (II)

which are respectively the 61-68 peptide and the 61-76 peptide of Kuwabara's tuberculin-active protein, have been synthesized.

The Inventors have shown that these two synthetic peptides possess tuberculin activity since they are able to induce a delayed-type allergic reaction in skin tests on Mycobacterium tuberculosis sensitized guinea-pigs as will be demonstrated hereafter. Accordingly, the present invention relates to a tuberculin-active peptide suitable for inducing a delayed-type allergic reaction in skin tests in mammals, comprising the above mentioned octapeptide (I) and/or hexadecapeptide (II).

According to another feature of the present invention, the octapeptide Asp-Gly-Gly-Ser-Glu-Ser-Glu-Gly is synthetized by a racemisation-free condensation involving the C-terminal glycine residue of the N-terminal tripeptide derivative of following formula III :

BOC-Asp(OBu$^t$)-Gly-Gly-OH (III)

to the C-terminal pentapeptide derivative represented by following formula IV :

H-Ser(Bu$^t$)-Glu(OBu$^t$)-Ser(Bu$^t$)-Glu(OBu$^t$)-Gly-OH, HCl (IV)

to give the octapeptide derivative represented by the following formula (Ia):

BOC-Asp(OBu$^t$)-Gly-Gly-Ser(Bu$^t$)-Glu(OBu$^t$)-Ser(-Bu$^t$)-Glu(OBu$^t$)-Gly-OH (Ia)

According to the present invention, the hexadecapeptide represented by above formula (II) is synthetized by a racemisation-free condensation of two octaoeptide derivatives one of which is represented by formula (Ia) to give a protected hexadecapeptide derivative of formula IIa:

BOC-Asp(OBu$^t$)-Gly-Gly-Ser (Obu$^t$)-Glu(Obu$^t$)-Ser (Bu$^t$)-Glu(OBu$^t$)Gly-Lys(Z)-Asn-Gly-Ser-Gln-Met-Arg(Tos)-Leu-Obzl (IIa)

which is freed from the protective groups by action of deprotective agents such as boron tris (trifluoroacetate) and thioanisole and purification by column chromotography, to obtain the deprotected hexadecapeptide of formula (II).

According to an embodiment of the synthesis process of the invention, the octapeptide of formula I is prepared starting from glycine methyl ester, preferably in its hydrochloride form, which is condensed with N$^\alpha$-Z-glutamic acid $\gamma$-t-butyl ester, in presence of N-methyl morpholine and ethyl chloroformate, into a protected dipeptide of formula V :

Z-Glu(OBu$^t$)-Gly-OMe (V), which, after hydrogenation, is condensed with N$^\alpha$-Z-serine $\beta$-t butyl ether to obtain the protected tripeptide represented by following formula (VI) :

Z-Ser(Bu$^t$)-Glu(OBu$^t$)-Gly-OMe (VI)

which, after hydrogenation, is coupled to N$^\alpha$-Z-glutamic acid $\gamma$-t-butyl ester to form the protected tetrapeptide represented by following formula (VII) :

Z-Glu(OBu$^t$)-Ser(Bu$^t$)-Glu(OBu$^t$)-Gly-OMe (VII)

which, after hydrogenation, is, in turn, condensed with N$^\alpha$-Z-serine $\beta$-t-butyl ether into following pentapeptide of formula VIII :

Z-Ser(Bu$^t$)-Glu(OBu$^t$)-Ser(Bu$^t$)-Glu(OBu$^t$)-Gly-OMe (VIII), said protected pentapeptide being then freed from the end methylester group by saponification of said last into the hydroxy group and then, after hydrogenation, condensed, preferably under the form of its hydrochloride, with a tripeptide represented by following formula IX :

BOC-Asp(OBu$^t$)-Gly-Gly-OH (IX)

preferably under the form of its 1-succinimidyl ester.

According to a preferred provision of said synthesis process, the N$^\alpha$-t-butyloxycarbonyl-$\beta$-t-butyl-L-aspartyl-glycyl-glycine of formula IX is obtained by coupling glycyl-glycine, preferably under the form of its benzylester, to N$^\alpha$-BOC-aspartic acid $\beta$-t-butylester.

According to another embodiment of the synthesis process of the invention, the hexadecapeptide of formula II is obtained starting from heptapeptide N$^\alpha$BOC-L-asparaginyl-glycyl-L-seryl-L-glutamyl-L-methionyl-($\omega$-tosyl)-L-arginyl-L-leucine, preferably in the form of its benzyl ester, which after being N$^\alpha$- deprotected by action of a deprotecting agent such as trifluoracetic acid, is coupled with N$^\alpha$-BOC-N$^\epsilon$-Z-lysine, preferably in the form of its succinimidyl ester, in the presence of N-methy-morpholine, to obtain the octapeptide represented by following formula X :

BOC-Lys(Z)-Asn-Gly-Ser-Glu-Met-Arg(tos)-Leu-Obzl (X)

which, after purification, is in turn N$^\alpha$-deprotected and then coupled to the octapeptide of formula (I) synthetized according to the present invention, preferably in the presence of triethylamine, N-hydroxysuccinimide and dicyclohexylcarbodiimide, to form the crude protected hexadecapeptide of formula (IIa) which is treated by a deprotecting agent comprising preferably thioanisole in combination with boron tris (trifluoracetate) in order to obtain the purified deprotected hexadecapeptide of formula (II).

The above and other objects, features and advantages of the present invention will become apparent from the following description which refers to examples of working out of the synthesis process according to the present invention and to tests for demonstrating the tuberculin activity of the octapeptide of formula (I) and of the hexadecapeptide of formula (II) according to the present invention. It is to be understood that said examples and tests are given solely by way of illustrations and are by no means to be considered as a limitation of the invention.

EXAMPLES

Example I—Synthesis of the octapeptide Asp-Gly-Gly-Ser-Glu-Ser-Glu-Gly of formula (I)

(1) First step : synthesis of Z-Glu(OBu$^t$)-Gly-OMe of formula (V)

A solution of $N^\alpha$-Z-glutamic acid $\gamma$-t-butyl ester (3.37 g, 10 mmol) and N-methyl morpholine (1.1 ml, 10 mmol) in dry tetrahydrofuran (50 ml) was cooled to $-15°$ C. and ethyl chloroformate (0.96 ml, 10 mmol) was added. After the solution was stirred for 2 min under a calcium chloride guard tube, a cold solution of glycine methyl ester hydrochloride (1.38 g, 11 mmol) and N-methyl morpholine (1.2 ml, 11 mmol) in dimethylformamide (25 ml) was added ; the reaction mixture was further stirred at $-10°$ C. for 30 min and then at room temperature for 2 h. The reaction mixture was diluted with ethyl acetate and washed with 5% aqueous sodium bicarbonate, 0.2 M potassium hydrogen sulfate and water. The organic solution was dried over magnesium sulfate and evaporated to dryness to give the product in the form of oil.

The thus prepared protected dipeptide of formula 1a V moved as a single spot on chromatograms obtained by silica-gel thin layer chromatography with chloroform-methanol (20:1) ($R_f$ 0.71) and was used without further purification. The yield was 3.76 g (92%).

(2) Second step : Synthesis of Z-Ser(Bu$^t$)-Glu(OBu$^t$)Gly-OMe of formula VI

The protected dipeptide of formula V obtained in the first step (4.08 g, 10 mmol) was dissolved in dimethylformamide (20 ml) and submitted to catalytic hydrogenolysis in the presence of 10% Pd-C (400 mg) and 6 N hydrochloric acid (1.7 ml, 10 mmol). At the end of the reaction the solution was diluted with methanol and adjusted to pH 4.5 with 1 N hydrogen chloride in methanol. The filtered solution was evaporated to dryness and the residual oil was triturated in ether and left under ether in the refrigerator overnight. After discarding the ether, the $\alpha$-t-butyl-L-glutamyl-glycine methyl ester hydrochloride ($R_f$ 0,47 obtained by silica-gel thin-layer chromatography with n-butanol-acetic acid-water 3:1:1) was obtained as an oil (3.05 g, 98%) and was coupled to $N^\alpha$-Z-serine $\beta$-t-butyl ether (2.89 g, 9.8 mmol) according to the procedure described for the preparation of dipeptide of formula (V). After the usual work-up, the product crystallized out from a concentrated ethyl acetate solution and was washed with ether and dried. The yield was 4.21 g (78%) [mp 114° to 116° C. (uncorrected); $(\alpha)_D^{22} = -13.4\pm0.5°$ (c=2.0, methanol); ($R_f$ 0,62 obtained by silica-gel thin layer chromatography with chloroform-methanol (20:1)] Analysis : calculated for $C_{27}H_{41}N_3O_9$: C, 58.79; H, 7.49; N, 7.62. Found : C, 58.73; H, 7.58; N, 7.44.

(3), Third step : Synthesis of Z-Glu(OBu$^t$)-Ser(Bu$^t$)-Glu(OBu$^t$)-Gly-OMe of formula VII.

The protected tripeptide of formula VI obtained in the 2nd step (5.52 g, 10 mmol) was dissolved in methanol (80 ml) and submitted to catalytic hydrogenolysis in the presence of 10% Pd-C and acetic acid (1 ml). At the end of the reaction the solution was adjusted to pH 4.5 with 1 N hydrogen chloride in methanol, filtered and evaporated to dryness. The $\beta$-t-butyl-L-seryl-$\gamma$-t-butyl-L-glutamyl-glycine methyl ester hydrochloride (4.36 g, 9.6 mmol) was obtained as a solid by trituration of the residual oil in ether:n-hexane (1:1) and was coupled to $N^\alpha$-Z-glutamic acid $\gamma$-t-butyl ester (3.24 g, 9.6 mmol) according to the procedure described for the preparation of the dipeptide of formula V. After the usual work-up, the product crystallized out from ethyl acetate on addition of an equal volume of n-hexane. The yield was 6.5 & g (92%) [mp 148° to 150° C. (uncorrected); $(\alpha)_D^{22} = -19.5\pm0.5°$ (c=2.0, methanol; $R_f$ 0,89 with n-butanolacetic acid-water (3:1:1) and $R_f$ 0,62 with chloroformmethanol (20:1) both by silica-gel thin layer chromatography]. Analysis : calculated for $C_{36}H_{56}N_4O_{12}$: C, 58.68; H, 7.66; N, 7.60. Found: C, 58.73; H, 7.69; N, 7.55.

(4) Fourth step : Synthesis of Z-Ser(Bu$^t$)-Glu(OBu$^t$)-Ser(Bu$^t$)-Glu(OBu$^t$)-Gly-OMe of formula VIII.

The protected tetrapeptide of formula VII obtained in the third step (3.68 g, 5 mmol) was dissolved in methanol (50 ml) and submitted to catalytic hydrogenolysis in the presence of 10% Pd-C and acetic acid (0.7 ml). At the end of the reaction the solution was adjusted to pH 4.5 with 1 N hydrogen chloride in methanol, filtered and evaporated to dryness. The $\gamma$-t-butyl-L-glutamyl-$\beta$-t-butyl-L-seryl-$\gamma$-t-butyl-L-glutamyl-glycine methyl ester hydrochloride (3.05 g, 4.8 mmol) crystallized out by trituration of the residual oil in ether and was coupled to $N^\alpha$-Z-serine $\beta$-t-butyl ether (1.42 g, 4.8 mmol) according to the procedure described for the preparation of dipeptide of formula V. The thick reaction mixture was diluted with ethyl acetate, washed as usual and evaporated to dryness. The solid residue was dispersed in ethanol, ether was added and the crystalline product was filtered and washed with ether. The yield was 3.88 g (92%) [mp 222° to 224° C.)(uncorrected); $(\alpha)_D^{22} = -18.5\pm0.5°$ (c=0.5, methanol); $R_f$, 0.93, from n-butenol-acetic acid-water (3:1:1) and $R_f$ 0,55 from chloroform-methanol(20:1)]. Analysis : calculated for $C_{43}H_{69}N_5O_{14}$: C, 58.69; H, 7.90; N, 7.96. Found: C, 58.71; H, 7.95; N, 8.03.

(5) Fifth step : Splitting of the protective end methyl grouo of Z-Ser(Bu$^t$)-Glu(OBu$^t$)-Ser(Bu$^t$)-Glu(OBu$^t$)-Gly-OMe of formula VIII.

The fully protected pentapeptide of formula VIII obtained in fourth step (4.40 g, 5 mmol) was dissolved in dioxane (160 ml) and water (16 ml) and the methyl ester was saponified at pH 11.5 by the addition of 1 N sodium hydroxide. At the end of the reaction, the product precipitated out on addition of 2 M potassium hydrogen sulfate to pH 2.5 and on dilution of the reaction mixture with water. After washing with water and drying, the product was recrystallized from ethyl acetate. The yield was 3.68 g (85%) of Z-Ser(Bu$^t$)-Glu (OBu$^t$)-Ser(Bu$^t$)-Glu(OBu$^t$)-Gly-OH [mp 210° to 212° C. (uncorrected); $R_f$, 0.68 (from n-butanol-acetic acid-water (3:1:1)]. Analysis : calculated for $C_{42}H_{67}N_5O_{14}$, $1H_2O$: C, 57.06; H, 7.87; N, 7.92. Found: C, 57.19; H, 7.80; N, 7.96.

(6) Sixth step : Preparation of the H-Ser(Bu$^t$)-Glu(OBu$^t$)-Ser(Bu$^t$)-Glu(OBu$^t$)-Gly-OH hydrochloride.

The partially protected pentapeptide of formula VIII obtained in fifth step (4.33 g, 5 mmol) was dissolved in methanol (250 ml) and water (5 ml) and was submitted to catalytic hydrogenolysis in the presence of 10% Pd-C and 1 N hydrochloric acid (5 ml, 5 mmol). The filtered solution was evaporated to a small volume. Repeated addition of ethanol and evaporation gave a gel, which on trituration in n-hexane yielded the product as an amorphous solid. The pentapeptide hydrochloride moved as a single spot on chromatograms [$R_f$, 0.54 from n-butanol-acetic acid-water (3:1:1)] and was used without further purification. The yield was 3.69 g (96%).

(7) Seventh step : Synthesis of the tripeptide BOC-Asp (OBu$^t$)-Gly-Gly-OBzl.

$N^\alpha$-t-butyloxycarbonyl-glycyl-glycine benzyl ester (3.22 g, 10 mmol) was dissolved in TFAOH -trifluoracetic acid - (30 ml) at 20° C. and left to stand for 2 h. After evaporation to dryness at 20° C. under reduced pressure, the glycyl-glycine benzyl ester trifluoracetate (3.23 g, 9.6 mmol) was obtained as a solid by trituration of the residual oil in ether and was coupled to $N^\alpha$-BOC-aspartic acid $\beta$-t-butyl ester (2.78 g, 9.6 mmol) according to the procedure described for the preparation of dipeptide of formula V. After the usual work-up, the product which could not be induced to crystallize, was obtained after evaporation of the solvent (ethyl acetate) and drying as a foam. Analysis: calculated for $C_{24}H_{35}N_3O_8$: C, 58.40; H, 7.15; N, 8.52. Found: C, 58.20; H, 7.19; N, 8.48. [$R_f$: 0.52 from chloroform: methanol (20:1)]. The yield was 4.50 g (95 %).

(8) Eigth step : Splitting of the protective end benzyle group of the tripeptide of step 7 to obtain BOC)Asp-(OBu$^t$)-Gly-Gly-OH of formula (IX).

The protected tripeptide synthetized in step 7 (4.93 g, 10 xmol) was dissolved in ethanol (150 ml) and submitted to catalytic hydrogenolysis in the presence of 10% Pd-C. The filtered solution was evaporated to dryness and the residual oil was dissolved in ether. On addition of dicyclohexylamine (2.0 ml, 10 mmol) the $N^\alpha$-BOC-$\beta$-t-butyl-L-aspartyl-glycyl-glycine dicyclohexylammonium salt crystallized out and was washed with ether. The yield was 5.26 g (90%) (mp 112° to 115° C. (uncorrected)). The product was suspended in ethyl acetate and was washed with 0.2 M potassium hydrogen sulfate and water. The organic solution was dried over magnesium sulfate and evaporated to dryness. The residual oil was redissolved in ether (20 ml) and n-hexane was added dropwise to the solution to precipitate the $N^\alpha$-BOC-$\beta$-t-butyl-L-aspartyl-glycyl-glycine of formula IX as a fine powder. The yield was 3.12 g (77%) [(mp 78° C. after sintering (uncorrected); $(\alpha)_D^{22}$ = $-4.9\pm0.5°$ (c=2.0, methanol); $R_f$: 0.59 from n-butanol-acetic acid-water (3:1:1) and $R_f$: 0.23 from chloroform:methanol (2:1)]. Analysis: calculated for $C_{17}H_{29}N_3O_8$: C, 50.61; H, 7.24; N, 10.42. Found: C, 50.55; H, 7.62; N, 9.85.

(9) Ninth step : Synthesis of BOC-Asp(OBu$^t$)-Gly-Gly-Ser(Bu$^t$)-Glu(OBu$^t$)-Ser(Bu$^t$)-Glu(OBu$^t$)-Gly-OH.

The tripeptide of formula IX obtained in step 8 (807 mg, 2 mmol) and N-hydroxysuccinimide (230 mg, 2 mmol) were dissolved in dioxane (10 ml) and ethyl acetate (2 ml). The solution was cooled to 0° C. and dicyclohexylcarbodiimide (412 mg, 2 mmol) in ethyl acetate (2 ml) was added. The reaction mixture was stirred 24 h at room temperature, the pH was adjusted to pH 3 with 0.2 M potassium hydrogen sulfate and the product was precipitated by addition of water, filtered and washed with 0.05 M potassium hydrogen sulfate and water. The dry, crude protected octapeptide was extracted with hot acetone and after centrifuging off an insoluble contaminant, the clear solution was evaporated to a small volume. On addition of n-hexane the partially protected octapeptide of the title precipitated out. The yield was 1.38 g (82%) [mp 210° C. with decomposition (uncorrected); $R_f$: 0.64 from chloroform : methanol (2:1)]. Analysis: calculated for $C_{51}H_{88}N_8O_{19}$: C, 54.82; H, 7.94; N, 10.03. Found C, 54.36; H, 7.91; N, 9.82. The amino acid analysis of an acid hydrolysate of the product gave: Asp, 0.95; Ser, 1.73; Glu, 2.09; Gly, 3.00.

(10) Tenth step : Splitting of the protective groups to obtain the octapeptide H-Asp-Gly-Gly-Ser-Glu-Ser-Glu-Gly-CH of formula (I).

The partially protected octapeptide obtained in step 9 (559 mg, 0.5 mmol) was dissolved in TFAOH (20 ml) at 20° C. and left to stand for 45 min. After evaporation to dryness at 20° C. under reduced pressure, the trifluoroacetate of the free octapeptide of formula (I) was obtained as a solid by trituration of the residual oil in ether. The yield was 421 mg (99%). The product was dissolved in 25 mM sodium chloride (1.4 ml). 1 N sodium hydroxide (approximately 250 µl) was added to bring the pH of the solution to pH 3.5 and the product was chromatographed on a column of Bio-Gel P-2 (1.6×84 cm) prepared in 25 mM sodium chloride. The chromatographically pure material which emerged at $V_e$ 75 to 85 ml, was lyophilized, redissolved in water (1 ml) and desalted on Bio-Gel P-2. The yield of the lyophilized pure octapeptide of formula (I) was 232 mg (63%) [$R_f$: 10.03 from n-butanol-acetic acid-water (3:1:1)]. Paper electrophoresis according to the procedure described by Offord [NATURE, 1966, 211, 591–593] gave a ninhydrin positive spot with the expected electrophoretic mobility (m=0.82). The amino acid analysis of an acid hydrolysate of the product gave: Asp, 0.97; Ser, 1.74; Glu, 2.03; Gly, 3.00.

Example II : Synthesis of the hexadecapeptide Asp-Gly-Gly-Ser-Glu-Ser-Glu-Gly-Lys-Asn-Gly-Ser-Gln-Met-Arg-Leu. (II)

(1) First step : Synthesis of BOC-Lys(Z)-Asn-Gly-Ser-Gln-Met-Arg(Tos)-Leu)OBzl of formula X.

$N^\alpha$-BOC-L-asparaginyl-glycyl-L-seryl-L-glutaminyl-L-methionyl-($\omega$-Tos)-L-arginyl-L-leucine benzyl ester (2.30 g; 2 mmol) was dissolved in TFAOH (60 ml) at 20° C. in the presence of thioanisole (11.7 ml, 100 mmol) and left to stand 1 h. After evaporation to dryness at 20° C. under reduced pressure, the $N^\alpha$-deprotected heptapeptide trifluoracetate [$R_f$, 0.33 from n-butanol-acetic acid-water (3:1:2)] was obtained as a solid (2.28 g, 98%) by thorough trituration of the residual oil in ether and was coupled at 20° C. for 24 h with $N^\alpha$-BOC-$N^\epsilon$-Z-lysine 1-succinimidyl ester [prepared as described by HARTTER, HOPPE SEILER'S Z. PHYSIOL. CHEM., 1976, 357(2), 1683–1693] (1.24 g, 2.6 mmol) in dimethylformamide (20 ml) in the presence of N-methyl morpholine (0.29 ml, 2.6 mmol). The crude octapeptide of formula (X) which precipitated out of the reaction mixture on addition of water, was dried, washed with ether and digested with hot ethanol. On cooling, the pure product was filtered and washed with absolute ethanol. The yield was 2.12 g (75%) [mp 218 to 220° C. (uncorrected); $R_f$, 0.60 from a butenol-acetic acid-water (3:1:1)]. Analysis: calculated for $C_{64}H_{94}N_{14}O_{18}S_2$: C, 54.46; H, 6.71; N, 13.89. Found: C, 54.07; H, 6.82; N, 13.75.

(2) Second step : Synthesis of the protected hexadecapeptide BOC-Asp(OBu$^t$)-Gly-Gly-Ser(Bu$^t$)-Glu(OBu$^t$)-Ser(Bu$^t$))Glu (OBu$^t$)-Gly-Lys(Z)-Asn-Gly-Ser-Gln-Met-Arg(Tos)-Leu-OBzl of formula IIa.

The octapeptide of formula X obtained in the first step (706 mg, 0.5 mmol) was dissolved in TFAOH (40 ml) at 20° C. under reduced pressure, the $N^\alpha$-deprotected octapeptide of formula X trifluoracetate (696 mg, 0.49 mmol) ($R_{f4}$, 0.39) was obtained as a solid by trituration of the residual oil in ether and was coupled to partially protected octapeptide of formula I obtained in the ninth step of Example I (547 mg, 0.49 mmol) in dimethylformamide (12 ml) at 0° C. in the presence of triethylamine (69 µl, 0.49 mmol), N-hydroxysuccinimide (56 mg, 0.49 mmol) and dicyclohexylcarbodiimide (101 mg, 0.49 mmol) (12). After 2 h at 0° C., the reaction mixture was left under stirring at room temperature for 5 days. By addition of water to the formed thick gel, the crude hexadecapeptide [$R_f$ 0.53 from n-butanol-acetic acid-water (3:1:1)] contaminated with dicyclohexyl urea, precipitated out. The yield was 1.21 g. Because of unfavorable solubility properties the crude protected hexadecapeptide of formula (IIa) was used without further purification.

(3) Third step : Splitting of the protective groups of the hexadecapeptide of formula IIa obtained in step (2) to obtain H-Asp-Gly-Gly-Ser-Glu-Ser-Glu-Gly-Lys-Asn-Gly-Ser-Gln-Met-Arg-Leu-OH of formula II.

The crude protected hexadecapeptide of formula IIa (603 mg, 0.25 mmol) was treated with thioanisole (1.47 ml, 12.5 mmol) and 1 M boron tris(trifluoracetate) in TFAOH (8) (25 ml, 25 mmol) was added at 0° C. After 5 min at 0° C., the reaction mixture was stirred at room temperature for 1.5 h and evaporated to dryness at 25° C. under reduced pressure. Water (100 ml) was added to the residual oil, the aqueous solution was extracted twice with ethyl acetate and after adjustment to pH 4.7 with 1 M sodium hydroxide, the solution was again extracted with ethyl acetate and evaporated to a small volume (10 ml) by azeotropic distillation under reduced pressure at 35° C. in the presence of ethanol. Part of the boric acid, formed as a byproduct, crystallized out, was filtered off and washed with water. The combined aqueous filtrates (16 ml) were desalted on a column of Sephadex G-15 and the salt-free, peptide-containing fractions were lyophilized. The yield was 240 mg (0.145 mmol). Paper electrophoresis at pH 6.5 showed this preparation to be a complex mixture of products among which the required hexadecapeptide of formula II could be identified by its Sakaguchi-positive reaction and by its complete disappearance after digestion with trypsin. The crude product (240 mg) was dissolved in 0.01 M phosphate buffer pH 7.0 (1.5 ml) and was chromatographed on a column of Sephadex G-25 Fine (1.6×85 cm) in the same solvent. The fractions enriched in hexadecapeptide of formula II ($V_e$ 92 to 104 ml) were lyophilized, dissolved in water (1.5 ml) and desalted on Sephadex G-15. After lyophilisation of the peptide-containing, salt-free fractions, the yield of the product was 116 mg (0.070 mmol). This material was chromatographed in two portions of 58 mg dissolved in 1 mM phosphate buffer pH 6.6 (2.5 ml) on a column of Cellex-D (2.6×43 cm) prepared in the same solvent. After washing the product on the column with 1 mM phosphate buffer (400 ml), a linear sodium chloride gradient was applied (830 ml 1 mM phosphate buffer pH 6.6 against 830 ml 0.4 M sodium chloride - 1 mM phosphate buffer pH 6.6). The fractions containing the hexadecapaptide ($V_E$ 235 to 309 ml) were lyophilized, desalted on Sephadex G-15 and again lyophilized. The total yield of the pure hexadecapeptide of formula II was 27 mg (16 μmol, 6.5%). Paper electrophoresis at pH 6.5 gave a single ninhydrin- and Sakaguchi-positive spot with the expected electrophoretic mobility (m=0.16). The amino acid analysis of an acid hydrolysate of the product gave: Arg, 1.00; Asp, 1.96; Glu, 3.03; Gly, 3.92; Leu, 1.01; Lys, 1.02; Met, 0.88; Ser, 2.51. Paper electrophoresis at pH 6.5 of a tryptic digest of the product gave three spots identified as: Leu (m=0.00); Asn-Gly-Ser-Gln-Met-Arg (m=0.34, Sakaguchi-positive); Asp-Gly-Gly-Ser-Glu-Ser-Glu-Gly-Lys (m=0.51).

DETERMINATION OF THE TUBERCULIN ACTIVITY OF THE OCTAPEPTIDE OF FORMULA I AND OF THE HEXADECAPEPTIDE OF FORMULA II

1. Tuberclin Tests

The tuberculin tests were carried out on guinea pigs sensitized 6 weeks before with heat-killed Mycobacterium tuberculosis strain Peuroïs or M. bovis BCG-Pasteur.

Doses of 200 μg of the octopeptide of formula (I) or of the hexadecapeptide of formula (II) in 100 μl of PBS buffer containing Tween 80, were administered intradermally in the ventral side of guinea pigs sensitized as mentioned above.

The appearance of a delayed-type tuberculin reaction was observed 24 h and 48 h after the injection.

(a) When a 200 μg dose of octapeptide of formula (I) in 100 μl of PBS was administered intradermally to guinea pigs sensitized with BCG, a weak skin reaction (4 mm) of low color intensity could be observed after 24 h.

(b) The administration of a 200 μg dose of hexadecapeptide of formula (II) to BCG-sensitized guinea pigs induced after 24 h a slightly stronger skin reaction (8 mm) but still of low color intensity.

In BCG-sensitized guinea pigs the administration of antigens of formulas (I) and (II) provoked little or no enduration, while the injection of 10 U of PPD to these animals induced, on the average, an erythematous area of 14 mm in diameter and an enduration of 16 mm.

(c) However, the administration of a 200 μg dose of hexadecapeptide of formula (II) to M. tuberculosis strain Peuroissensitized guinea pigs, induced after 24 h a normal tuberculin-type skin reaction with on the average, an erythematous area of 11 mm in diameter and an enduration of 12 mm.

In these animals, 10 U of PPD provoked an erythema of 14 mm and an enduration of 16 mm. The histological examination of biopsies of the skin, showed that the reaction induced by PPD and by the hexadecapeptide of formula (II) were similar, except that the reaction caused by the synthetic peptide contained a higher percentage of polymorphonuclear cells.

These tests show, accordingly, that the octapeptide of formula (I) and the hexadecapeptide of formula (II) according to the invention induce a delayed type allergic reaction, i.e. a tuberculin-type reaction and are able to discriminate, in skin tests, animals sensitized with different species of mycobacteria. 2. Radioimmunoassays have been performed in order to control whether the purified protein derivative (PPD), i.e. the complex mixture of proteins of unknown compositions which is excreted into the culture medium of M. tuberculosis, as mentioned hereinabove, and which is in wide use as a tuberculin-active preparation, cross-reacts with the synthetic octapeptide by using $^{125}$I-labeled octapeptide and an anti-octapeptide antiserum.

The radioimmunoassays were performed using 0.05 M tris (hydroxymethyl) aminomethane (pH 7,4) containing 0.15 M sodium chloride, 0,1% sodium azide and 0.5% BSA as buffet and an anti-octapeptide antiserum diluted (1: 2,000) with buffet to give 50% bound labeled octapeptide of formula (I) in the absence of unlabeled standard.

For perfoming the radioimmunoassays :

(1) A BSA-octapeptide conjugate was prepared from BSA (25 mg) and octapeptide of formula I (10 mg) by reaction with glutaraldehyde in the way described in the reference cited above (J. SAVRDA, "Infection and Immunity" Dec. 1980, vol. 30, No. 3, p 686-693). The amount of octapeptide coupled to BSA was 17 mol per mol of BSA.

(2) an anti-octapeptide antiserum was prepared as follows: Rabbits were immunized by multisite subcutaneous injections of 2mg of the BSA-octapeptide conjugate prepared according to (1) hereinabove, in the presence of MDP and Freund incomplete adjuvant. Each rabbit received three injections over a period of 2 weeks and booster injections every 2 months. The antisera were collected 10 days after injection and then collected every 2 weeks.

(3) Preparation of the $^{125}$I - labeled octapeptide.

A 5 μg portion of the octapeptide of formula (I) in 10 μl of 0.1 M borate buffer pH 8.6, was added to 500 μCi og Bolton-Hunter reagent - $^{125}$I-labeled 3-(4-hydroxyphenyl) propionic acid N-succinimidyl ester - (specific activity, ca. 2,000 Ci/mmol); the reaction mixture was left at 0° C. for 40 min and was developed on silica gel thin-layer chromatography in a solvent system n-butanol-acetic acid-water (3:1:1). The immunoreactive radioactive band ($R_f$ 0.55 from the above solvent system) was eluted with approximately 5 ml of a watermethanol (1:1) mixture. This stock solution of labeled peptide (400,000 cpm/10 μl) was kept at <0° C. before use.

(4) Enzymatic digestions.

Solutions, 1%, of octapeptide (I) hexadecapeptide II or PPD (PPD-neutre Pasteur) were digested with trypsin and the digests passed on Sepharose-bound soybean trypsin inhibitor. The resulting solutions were further treated with carboxypeptidase B, with an exopeptidase-to-substrate weight ratio of 1:100 at 25° C. for 2 h and then heated for 5 min at 100° C. These stock solutions (800 μg of hydrolyzed substrate per 100 μl) were diluted before use with 0.05 M tris(hydroxymethyl) aminomethane buffer (pH 7.4), containing 0.15 M sodium chloride, 0.1% sodium azide and 0.5% BSA.

M. tuberculosis strain Aoyama/B- and M. bovis BCG-Pasteur-extracts were likewise digested with trypsin and carboxypeptidase B, except that the concentration of the substrate (protein) was 0.04% and 0.6% respectively.

(5) Results

An antiserum capable of binding 50% of a 10,000-cpm dose of $^{125}$I-labeled octapeptide of formula (I) at a 1:2,000 dilution, prepared as described in (2) hereinabove, and showing a good affinity for this octapeptide antigen, was selected for radioimmunoassays. The amounts of unlabeled octapeptide of formula (I), undigested or trypsin- and carboxypeptidase B-digested hexadecapeptide of formula (II), PPD, Aoyama/B or BCG extraxts, required to displace half of the label in radioimmunoassays, are summarized in the following Table I :

TABLE I 250 pg of octapeptide (X)
Asp—Gly
61    68

250 pg of Tr— and COB—digested octapeptide (X) (control)
Asp—Gly
61    68

500 ng of hexadecapeptide (XIII)
Asp—Gly—Lys—Asn—Met—Arg—Leu
61    68       70    74    76

TABLE I-continued 150 ng of Tr—digested hexadecapeptide (XIII)
Asp—Gly—Lys.Asn—Met—Arg.Leu
61    68       70    74

700 pg of Tr— and COB—digested hexadecapeptide (XIII)
Asp—Gly.Lys.Asn—Met.Arg.Leu
61    68       70    74

150 μg of Tr— and COB—digested PPD
180 μg of Tr— and COB—digested Abyama/B extract
900 μg of Tr— and COB—digested BCG extract This Table shows that only 250 pg of cold synthetic octapeptide of formula (I) were required to displace half of the label in radioimmunoassays using antibodies raised against this peptide, conjugated through its N-terminal α-amine to BSA, and the N$^{\alpha}$-$^{125}$I-labeled octapeptide of formula (I). However, the advantage of this good sensitivity of the assays was to some extent diminished by the great specificity of the antibodies which were strongly directed to the C-terminal end of the octapeptide of formula (I). Thus, when the C-terminal glycine residue of said octapeptide was implicated in a peptide linkage, as in the case of the hexadecapeptide of formula (II), the observed level of recognition, taking into account the molecular weight of said hexadecapeptide, was only 0.1%, 500ng of this antigen being required to displace half of the label. When the C-terminal glycine residue of octapeptide of formula (I) was implicated in a peptide linkage with only a single lysine residue, as in the case of the trypsin-digested hexadecapeptide of formula (II), the level of recognition was still only 0.4%. Only after further carboxypeptidase B-digestion was the level of recognition restored to 80% of that of octapeptide of formula (I), the small loss of potency in cross-reactivity certainly being due to incomplete digestion of the hexadecapeptide of formula (II) by the proteases. The very low levels of cross-reactivity between trypsin- and carboxypeptidase B-digested PPD, Aoyama/ or BCG extract, and the octapeptide of formula (I) in radioimmunoassays are therefore to some degree underestimated, as the action of the proteases on these substrates was probably not complete. The observed cross-reaction of trypsin- and carboxypeptidase B- digested PPD with the octapeptide of formula (I) is however of the same order of magnitude as the one observed in the previous study performed by I. SAVRDA (loc. cited) using the $^{125}$I-labeled heptapeptide and an anti-heptapeptide antiserum. The similitude of these results seems therefore to indicate that the sequence given by Kuwabara for the heptapeptide described in said reference and for the octapeptide 61-68 are correct, as well as the structure of the synthetic peptides according to the present invention, since the ratio of these peptides in PPD, even in the form of larger protein fragments, can be expected to be 1:1. These considerations lead to believe that the known heptapeptide 70-76 described in the reference cited does not represent an antigenic determinant responsible for the delayed-type allergic tuberculin reaction, as was already reported in said reference and that the reason for the discrepancy between the results mentioned in said reference and those reported by Kuwabara does not reside in an incorrect sequence of the heptapeptide. The exceedingly low levels of cross-reactivity on radioimmunoassays, observed with the trypsinand carboxypeptidase B- digested extracts from Aoyama/B and BCG strains, do not permit much interpretation as the reported amounts of antigen added in radioimmunoassays (see Table I above) are only extrapolated values from inhibition curves. However, it emerges from these results that a better cross-reactivity has been found in M. tuberculosis extracts, either PPD or Aohama/B, than in the M. bovis BCG extract, which may be related with a difference in concentration of the octapeptide 61-68 in these extracts.

It results from the foregoing that the synthetic octapeptide of formula (I) and hexadecapeptide of formula (II) possess a tuberculin-activity which allows their use as specific tuberculin-active products for the diagnosis of tuberculous infections or diseases and allows to contemplate the substitution of the known wide-used tuberculinactive preparations obtained from products excreted into the culture media of Mycobacterium Tuberculosis, which are less specific, by the synthetic peptides according to the present invention.

What we claim is:

1. A synthetic peptide of formula (II):

Asp-Gly-Gly-Ser-Glu-Ser-Glu-Gly-Lys-Asn-Gly-Ser-Glu-Met-Arg-Leu.    (II)

2. A synthetic peptide of formula (I):

Asp-Gly-Gly-Ser-Glu-Ser-Glu-Gly.    (I)

3. An injectable, tuberculin-active composition characterized in that said composition comprises an amount of the synthetic peptide of formula (II) of claim 1 effective to induce a delayed-type tuberculin reaction.

4. An injectable tuberculin-active composition characterized in that said composition comprises an amount of the synthetic peptide of formula (I) of claim 2 effective to induce a delayed-type tuberculin reaction.

* * * * *